United States Patent
Asai et al.

(10) Patent No.: US 6,693,115 B2
(45) Date of Patent: Feb. 17, 2004

(54) ACID ADDITION SALTS OF HYDROPYRIDINE DERIVATIVES

(75) Inventors: Fumitoshi Asai, Tanashi (JP); Taketoshi Ogawa, Tokyo (JP); Hideo Naganuma, Tokyo (JP); Naotoshi Yamamura, Nishitokyo (JP); Teruhiko Inoue, Ube (JP); Kazuyoshi Nakamura, Onoda (JP)

(73) Assignees: Sankyo Company, Limited, Tokyo (JP); Ube Industries Ltd., Ube (JP)

( * ) Notice: Subject to any disclaimer, the term of this patent is extended or adjusted under 35 U.S.C. 154(b) by 0 days.

(21) Appl. No.: 10/329,629

(22) Filed: Dec. 26, 2002

(65) Prior Publication Data

US 2003/0134872 A1 Jul. 17, 2003

Related U.S. Application Data

(63) Continuation of application No. PCT/JP01/05764, filed on Jul. 3, 2001.

(30) Foreign Application Priority Data

| Jul. 6, 2000 | (JP) | 2000-205396 |
| Sep. 4, 2000 | (JP) | 2000-266780 |

(51) Int. Cl.$^7$ .................. A61K 31/4365; C07D 495/04; A61P 7/02
(52) U.S. Cl. ........................ 514/301; 546/114
(58) Field of Search ............................ 514/301; 546/114

(56) References Cited

U.S. PATENT DOCUMENTS

| 4,141,894 A | * 2/1979 | Zimmerman | 540/593 |
| 5,288,726 A | 2/1994 | Koike et al. | |
| 5,342,851 A | * 8/1994 | Sanfilippo et al. | 514/370 |

FOREIGN PATENT DOCUMENTS

| EP | 0 192 535 A1 | 8/1986 |
| EP | 0 542 411 A2 | 5/1993 |
| JP | 64-022847 | 1/1989 |
| JP | 7-188168 | 7/1995 |

OTHER PUBLICATIONS

Berge SM et al. Jounal of Pharmaceutical Sciences (19770, 66(1), 1–19.*
Fumitoshi Asai et al., "CS–747, a New Platelet ADP Receptor Antagonist", *Annu. Rep. Sankyo. Res. Laboratory*, (1999), vol. 51, pp. 1–44.
Atsuhiro Sugidachi et al., "The In Vivo Pharmaceutical Profile of CS–747, A Novel Antiplatelet Agent with Platelet ADP Receptor Antagonist Properties", *Br. J. Pharmacol.*, (2000), vol. 168, pp. 178–195.
Born et al., "The Aggregation of Blood Platelets", *J. Physiol.*, (1963), vol. 168, pp. 178–195.

* cited by examiner

*Primary Examiner*—Evelyn Mei Huang
(74) *Attorney, Agent, or Firm*—Frishauf, Holtz, Goodman & Chick, P.C.

(57) ABSTRACT

Acid addition salts of 2-acetoxy-5-(α-cyclopropyl-carbonyl-2-fluorobenzyl)-4,5,6,7-tetrahydrothieno[3,2-c]-pyridine. The acid addition salts of tetrahydrothienopyridine derivatives of the present invention exhibit excellent oral absorption, metabolization into the active compound, and platelet aggregation-inhibiting effects, low toxicity, and excellent storage and handling stabilities, and are useful as medicaments, preferably preventive or therapeutic agents (particularly therapeutic agents) for diseases caused by a thrombus or an embolus, still more preferably preventive or therapeutic agents (particularly therapeutic agents) for thrombosis or embolism.

15 Claims, No Drawings

ACID ADDITION SALTS OF HYDROPYRIDINE DERIVATIVES

CROSS-REFERENCE TO RELATED APPLICATION

This application is a continuation application of International application PCT/JP01/05764 filed Jul. 3, 2001, the entire contents of which are hereby incorporated by reference herein.

BACKGROUND OF THE INVENTION

1. Field of the Invention

The present invention relates to acid addition salts of 2-acetoxy-5-(α-cyclopropylcarbonyl-2-fluorobenzyl)-4,5,6,7-tetrahydrothieno[3,2-c]pyridine (preferably the hydrochloride or maleate) which exhibit excellent oral absorption, metabolization into the active compound, and activity in inhibition of platelet aggregation, and are useful as therapeutic or prophylactic agents for thrombus formation-induced or embolization-induced diseases.

2. Background Information

In EP-542411 (Japanese Patent Application Publication No. Hei 6-411239) it is described that 2-acetoxy-5-(α-cyclopropylcarbonyl-2-fluorobenzyl)-4,5,6,7-tetrahydrothieno[3,2-c]pyridine and derivatives thereof, which are antagonists of receptors of adenosine diphosphate (hereinafter referred to as "ADP"), exhibit excellent activity in inhibition of platelet aggregation and are useful as antithrombotic or antiembolic agents.

SUMMARY OF THE INVENTION

For many years the present inventors have earnestly studied the pharmacological activity of various hydropyridine derivatives in order to discover compounds having excellent activity in inhibition of platelet aggregation. The present inventors have found that acid addition salts of 2-acetoxy-5-(α-cyclopropylcarbonyl-2-fluorobenzyl)-4,5,6,7-tetrahydrothieno[3,2-c]pyridine (preferably the hydrochloride or maleate) exhibit excellent oral absorption, metabolization into the active compound, activity in inhibition of platelet aggregation, low toxicity, and excellent storage and handling stability, and are useful as medicaments (preferably useful as therapeutic or prophylactic agents (preferably therapeutic agents)) for thrombus formation-induced or embolization-induced diseases (preferably thrombosis or embolism).

The present invention provides acid addition salts of 2-acetoxy-5-(α-cyclopropylcarbonyl-2-fluorobenzyl)-4,5,6,7-tetrahydrothieno[3,2-c]pyridine (preferably the hydrochloride or maleate), which exhibit excellent activity in inhibition of platelet aggregation; processes for the preparation thereof; and medicaments containing them which are useful as therapeutic or prophylactic agents (preferably therapeutic) for thrombus formation-induced or embolization-induced diseases, and are preferably useful as therapeutic or prophylactic agents (preferably therapeutic agents) for thrombosis or embolism.

DETAILED DESCRIPTION OF THE INVENTION

The present invention relates to acid addition salts of 2-acetoxy-5-(α-cyclopropylcarbonyl-2-fluorobenzyl)-4,5,6,7-tetrahydrothieno[3,2-c]pyridine (hydrochloride or maleate) and relates to medicaments containing acid addition salts of 2-acetoxy-5-(α-cyclopropylcarbonyl-2-fluorobenzyl)-4,5,6,7-tetrahydrothieno[3,2-c]pyridine (hydrochloride or maleate) as an active ingredient.

The acid moiety of acid addition salts of 2-acetoxy-5-(α-cyclopropylcarbonyl-2-fluorobenzyl)-4,5,6,7-tetrahydrothieno[3,2-c]pyridine is, for example, an inorganic acid such as sulfuric acid, hydrochloric acid, nitric acid, phosphoric acid; or an organic acid such as trifluoroacetic acid, maleic acid, methanesulfonic acid, p-toluenesulfonic acid, and preferably hydrochloric acid or maleic acid.

2-Acetoxy-5-(α-cyclopropylcarbonyl-2-fluorobenzyl)-4,5,6,7-tetrahydrothieno[3,2-c]pyridine hydrochloride of the present invention has the following formula:

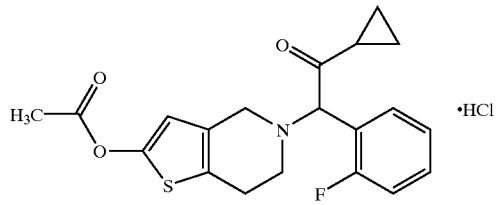

2-Acetoxy-5-(α-cyclopropylcarbonyl-2-fluorobenzyl)-4,5,6,7-tetrahydrothieno[3,2-c]pyridine maleate has the following formula:

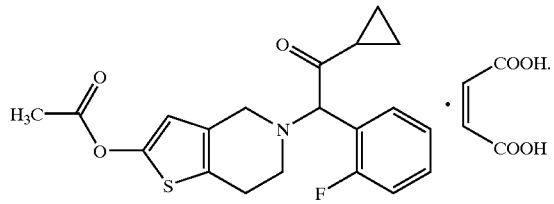

Acid addition salts of 2-acetoxy-5-(α-cyclopropylcarbonyl-2-fluorobenzyl)-4,5,6,7-tetrahydrothieno[3,2-c]pyridine have an asymmetric carbon in their molecule and in each compound two isomers having R and S configurations can exist. The present invention encompasses the individual isomers and mixtures of these isomers in optional proportions. An optically active isomer of acid addition salts of 2-acetoxy-5-(α-cyclopropylcarbonyl-2-fluorobenzyl)-4,5,6,7-tetrahydrothieno[3,2-c]pyridine of the present invention can be prepared using an optically active starting material or is isolated from a racemic mixture of synthetically prepared acid addition salts of 2-acetoxy-5-(α-cyclopropylcarbonyl-2-fluorobenzyl)-4,5,6,7-tetrahydrothieno[3,2-c]pyridine by a conventional optical resolution.

In some cases, when acid addition salts of 2-acetoxy-5-(α-cyclopropylcarbonyl-2-fluorobenzyl)-4,5,6,7-tetrahydrothieno[3,2-c]pyridine are allowed to stand in contact with the atmosphere or are recrystallized, they may absorb water or may take up water to form a hydrate. The present invention encompasses these hydrates.

Acid addition salts of 2-acetoxy-5-(α-cyclopropylcarbonyl-2-fluorobenzyl)-4,5,6,7-tetrahydrothieno[3,2-c]pyridine are prepared in the presence or absence of an inert solvent (preferably in an inert solvent) by addition of 2-acetoxy-5-(α-cyclopropylcarbonyl-2-fluorobenzyl)-4,5,6,7-tetrahydrothieno[3,2-c]pyridine, which is synthesized by a method described in EP-542411, to an acid (preferably hydrochloric acid, hydrogen chloride (gas), or maleic acid; more preferably concentrated hydrochloric acid or maleic acid; most preferably concentrated hydrochloric acid); or in the presence or absence of an inert solvent (preferably in an inert solvent) by dropwise addition or addition of an acid (preferably hydrochloric acid, hydrogen chloride (gas), or maleic acid; more preferably concentrated hydrochloric acid or maleic acid; most preferably concentrated hydrochloric acid) at one or more times to 2-acetoxy-5-(α-cyclopropylcarbonyl-2-fluorobenzyl)-4,5,6,7-tetrahydrothieno[3,2-c]pyridine. In this procedure, if necessary, seed crystals of said salt can be added.

The solvent used in the above reaction is not particularly restricted provided that it has no adverse effect on the reaction and it can dissolve the starting material to some extent. Examples of such solvents include aliphatic hydrocarbons such as hexane, cyclohexane, heptane, ligroin or petroleum ether; aromatic hydrocarbons such as benzene, toluene or xylene; halogenated hydrocarbons such as dichloromethane, chloroform, carbon tetrachloride, 1,2-dichloroethane, chlorobenzene or dichlorobenzene; ether derivatives such as diethyl ether, diisopropyl ether, tetrahydrofuran, dioxane, dimethoxyethane or di(ethyleneglycol)dimethyl ether; ketone derivatives such as acetone, methyl ethyl ketone or diethyl ketone; ester derivatives such as ethyl acetate, propyl acetate or butyl acetate; carboxylic acid derivatives such as acetic acid or propionic acid; or nitrile derivatives such as acetonitrile or propionitrile. For the preparation of the hydrochloride, the preferred solvents are ether derivatives, ketone derivatives, ester derivatives, carboxylic acid derivatives or nitrile derivatives; more preferred solvents are tetrahydrofuran, dioxane, acetone, methyl ethyl ketone, ethyl acetate, acetic acid or acetonitrile; still more preferred solvents are tetrahydrofuran, dioxane, acetic acid or acetone. Acetone is the most preferred. On the other hand for the preparation of the maleate, the preferred solvents are ether derivatives, ketone derivatives, ester derivatives or nitrile derivatives; more preferred solvents are tetrahydrofuran, dioxane, acetone, methyl ethyl ketone, ethyl acetate, or acetonitrile; still more preferred solvents are tetrahydrofuran, dioxane or acetone. Acetone is the most preferred.

The reaction temperature will vary depending on the reagent, the solvent and the like, and usually is from −20° C. to 100° C., preferably from 0° C. to 70° C. With respect to the hydrochloride, the reaction temperature is preferably from 30° C. to 60° C. and more preferably from 40° C. to 55° C.

The reaction time will vary depending on the reagent, the solvent, the reaction temperature and the like, and usually is from 5 minutes to 10 hours, preferably 10 minutes to 5 hours.

With respect to the preparation of the maleate, the reaction is preferably carried out by addition of 2-acetoxy-5-(α-cyclopropylcarbonyl-2-fluorobenzyl)-4,5,6,7-tetrahydrothieno[3,2-c]pyridine to a solution of maleic acid in acetone between 0 and 70° C. followed by allowing to stand at said temperature for 1 hour to 3 hours.

With respect to the preparation of the hydrochloride, the reaction is preferably carried out by addition or dropwise addition of the required amount of concentrated hydrochloric acid (usually equimolar with respect to the thienopyridine derivative) to a solution of 2-acetoxy-5-(α-cyclopropylcarbonyl-2-fluorobenzyl)-4,5,6,7-tetrahydrothieno[3,2-c]pyridine in acetone between 0° C. and 70° C. (preferably between 35 and 60° C.) followed by allowing to stand at said temperature for 30 minutes to 3 hours.

More preferably the reaction is carried out by dropwise addition of half of the required amount of concentrated hydrochloric acid (usually equimolar with respect to the thienopyridine derivative) to a solution of the thienopyridine derivative in acetone between 35° C. and 60° C. (preferably between 40 and 55° C.) over from 2 minutes to 10 minutes, with addition of seed crystals of said salt if necessary, followed by allowing to stand at said temperature for 30 minutes to 2 hours; and then by further dropwise addition of the remaining required amount of concentrated hydrochloric acid to the reaction mixture over from 30 minutes to 2 hours followed by allowing to stand at said temperature for 1 hour to 3 hours.

After the reaction, the acid addition salts of 2-acetoxy-5-(α-cyclopropylcarbonyl-2-fluorobenzyl)-4,5,6,7-tetrahydrothieno[3,2-c]pyridine can be isolated from the reaction mixture by conventional methods. For example, after the reaction, the resulting crystals are isolated by filtration to afford the desired product or the solvent of the reaction mixture is evaporated to afford the desired product. The product, if necessary, can be purified by recrystallization, reprecipitation or chromatography.

The acid addition salts of 2-acetoxy-5-(α-cyclopropylcarbonyl-2-fluorobenzyl)-4,5,6,7-tetrahydrothieno[3,2-c]pyridine of the present invention exhibit excellent oral absorption, metabolism into the active compound, and activity in inhibition of platelet aggregation, low toxicity, and further excellent storage and handling stability, therefore, they are useful as prophylactic or therapeutic agents (preferably therapeutic agents) for thrombus formation-induced or embolization-induced diseases; more preferably prophylactic or therapeutic agents (preferably therapeutic agents) for thrombosis or embolism. The medicaments described above are preferably for a warm blooded animal, more preferably a human.

When the acid addition salts of 2-acetoxy-5-(α-cyclopropylcarbonyl-2-fluorobenzyl)-4,5,6,7-tetrahydrothieno[3,2-c]pyridine of the present invention are used as therapeutic or prophylactic agents for the diseases as described above, they can be administered alone or as a mixture with pharmaceutically acceptable excipients, diluents and the like, in various dosage forms such as tablets, capsules, granules, powders, syrups or the like for oral administration; and injections, suppositories or the like for parenteral administration.

Each of the above formulations can be prepared by well-known methods using additives (i.e., pharmaceutically acceptable carriers) for the formulation such as excipients, lubricants, binders, disintegrants, emulsifiers, stabilizers, corrigents, and diluents.

Examples of excipients include organic excipients, for example sugar derivatives such as lactose, sucrose, glucose, mannitol or sorbitol; starch derivatives such as corn starch, potato starch, α-starch or dextrin; cellulose derivatives such as crystalline cellulose; acacia; dextran; pullulan; and inorganic excipients; for example silicate derivatives such as light silicic acid anhydride, synthetic aluminum silicate, calcium silicate, or magnesium aluminate metasilicate; phosphate derivatives such as calcium hydrogenphosphate; carbonate derivatives such as calcium carbonate; sulfate derivatives such as calcium sulfate, or the like.

Examples of lubricants include stearic acid; metal stearate derivatives such as calcium stearate or magnesium stearate; talc; waxes such as beeswax or spermaceti; boric acid; adipic acid; sulfate derivatives such as sodium sulfate; glycol; fumaric acid; sodium benzoate; DL-Leucine; lauryl sulfate derivatives such as sodium lauryl sulfate or magnesium lauryl sulfate; silicic acid derivatives such as silicic anhydride or silicic acid hydrate; and starch derivatives as described in the excipients above.

Examples of binders include hydroxypropylcellulose, hydroxypropylmethylcellulose, polyvinylpyrrolidone, macrogol (trade name) or excipients as described in the excipients above.

Examples of disintegrants include cellulose derivatives such as lower-substituted hydroxypropylcellulose, carboxymethylcellulose, calcium carboxymethylcellulose or internally cross-linked sodium carboxymethylcellulose; chemically modified starch or cellulose derivatives such as carboxymethylstarch or sodium carboxymethylstarch; cross-linked polyvinylpyrrolidine; and starch derivatives as described above.

Examples of emulsifiers include colloidal clay such as bentonite or veegum; metal hydroxides such as magnesium hydroxide or aluminum hydroxide; anionic surfactants such as sodium lauryl sulfate or calcium stearate; cationic surfactants such as benzalkonium chloride; non-ionic surfactants such as polyoxyethylene alkyl ether, polyoxyethyene sorbitan esters of fatty acids or sucrose esters of fatty acids.

Examples of stabilizers include para-hydroxybenzoic acid ester derivatives such as methylparaben or propylparaben; alcohol derivatives such as chlorobutanol, benzyl alcohol or phenethyl alcohol; benzalkonium chloride; phenol derivatives such as phenol or cresol; thimerosal; dehydroacetic acid or sorbic acid.

Examples of corrigents include sweeteners, souring agents, flavorings or the like which are conventionally used.

The specific dose of a compound of the present invention will be varied according to the severity of the patient's symptoms, age and the like. For oral administration the quantity of active ingredient in a unit dosage may be in the range of 0.1 mg (preferably 1 mg) to 1000 mg (preferably 500 mg). A unit dose for intravenous administration may be in the range of 0.01 mg (preferably 0.1 mg) to 500 mg (preferably 250 mg) of a compound of the present invention.

The unit dose may be administered to a human adult from 1 to 7 times per a day for a period of from 1 to 7 days depending on the severity of the patient's symptoms.

EXAMPLES

The following examples, reference examples, test examples and formulation examples are intended to further illustrate the present invention and are not intended to limit the scope of this invention.

Example 1

2-Acetoxy-5-(α-cyclopropylcarbonyl-2-fluorobenzyl)-4,5,6,7-tetrahydrothieno[3,2-c]pyridine hydrochloride (crystal A).

To a solution of 2-acetoxy-5-(α-cyclopropylcarbonyl-2-fluorobenzyl)-4,5,6,7-tetrahydrothieno[3,2-c]pyridine (10 g) obtained in Reference example 1 in acetone (150 ml) was added dropwise concentrated hydrochloric acid (36%, 2.71 g) with stirring at room temperature (25° C.). A small amount of seed crystals of the desired product (crystal A prepared by other procedure) was added to the solution and then the mixture was stirred for 90 minutes at the same temperature. The resulting crystals were separated by filtration and the crystals were washed with a small amount of acetone and then dried at 50° C. under reduced pressure for 4 hours to give the title compound as white crystals (8.1 g, yield 74%) (crystal A).

mp: 133–136° C.;

$^1$H NMR (CDCl$_3$) δppm: 0.92–0.99 (1H, m), 1.05–1.16 (2H, m), 1.23–1.34 (1H, m), 1.84–1.95 (1H, m), 2.26 (3H, s), 3.07–3.23 (2H, m), 3.57–4.39 (4H, m), 6.04 (1H, s), 6.45 (1H, brs), 7.37–7.57 (3H, m), 7.66–7.75 (1H, m);

Mass (CI, m/z): 374 (M$^+$+1);

IR (KBr) ν$_{max}$cm$^{-1}$: 1762, 1720.

Example 2

2-Acetoxy-5-(α-cyclopropylcarbonyl-2-fluorobenzyl)-4,5,6,7-tetrahydrothieno[3,2-c]pyridine maleate.

To a solution of maleic acid (4.43 g) in acetone (60 ml) was added 2-acetoxy-5-(α-cyclopropylcarbonyl-2-fluorobenzyl)-4,5,6,7-tetrahydrothieno[3,2-c]pyridine (15.0 g) obtained in Reference example 1, then the mixture was stirred at room temperature (25° C.) for 2 hours. The resulting crystals were separated by filtration and washed with a small amount of acetone and then dried at 50° C. under reduced pressure for 4 hours to give the title compound as white crystals (17.1 g, yield 92%)

mp: 171–172° C.;

$^1$H NMR (CD$_3$OD) δppm: 0.89–0.97 (1H, m), 1.02–1.09 (2H, m), 1.14–1.23 (1H, m), 1.94–2.03 (1H, m), 2.25 (3H, s), 3.00–3.09 (2H, m), 3.33–3.50 (2H, m), 3.88 (1H, d, J=14.9 Hz), 4.05 (1H, d, J=14.9 Hz), 5.70 (1H, s), 6.25 (2H, s), 6.40 (1H, s), 7.30–7.42 (2H, m), 7.45–7.52 (1H, m), 7.56–7.66 (1H, m);

Mass (CI, m/z): 374 (M$^+$+1);

IR (KBr) ν$_{max}$cm$^{-1}$: 1782, 1713.

Example 3

2-Acetoxy-5-(α-cyclopropylcarbonyl-2-fluorobenzyl)-4,5,6,7-tetrahydrothieno[3,2-c]pyridine Hydrochloride (Crystal B1)

To a solution of 2-acetoxy-5-(α-cyclopropylcarbonyl-2-fluorobenzyl)-4,5,6,7-tetrahydrothieno[3,2-c]pyridine (10 g) obtained in Reference example 1 in acetone (100 ml) was added dropwise concentrated hydrochloric acid (36%, 2.71 g) over 1 minute with stirring at 40° C. The reaction mixture was stirred at the same temperature for 60 minutes (crystals started to precipitate after 10 minutes from the addition of concentrated hydrochloric acid). The resulting crystals were separated by filtration and the crystals were washed with acetone (20 ml) and then dried at 60° C. under reduced pressure for 2 hours to give the title compound as white crystals (9.72 g, yield 89%) (crystal B1) which exhibit more excellent storage stability than crystal A.

mp: 166–174° C.;

Mass (CI, m/z): 374 (M$^+$+1);

IR (KBr) ν$_{max}$cm$^{-1}$: 1758, 1690.

Example 4

2-Acetoxy-5-(α-cyclopropylcarbonyl-2-fluorobenzyl)-4,5,6,7-tetrahydrothieno[3,2-c]pyridine hydrochloride (crystal B2)

To a solution of 2-acetoxy-5-(α-cyclopropylcarbonyl-2-fluorobenzyl)-4,5,6,7-tetrahydrothieno[3,2-c]pyridine (50 g) obtained in Reference example 1 in acetone (750 ml) was added dropwise concentrated hydrochloric acid (36%, 6.78 g) over 5 minutes with stirring at 40° C. Crystals of B1 (0.1 g) obtained in Example 3 were added to the reaction mixture as seed crystals and the resulting mixture was stirred at the same temperature for 60 minutes. To the resulting mixture was further added dropwise concentrated hydrochloric acid (36%, 6.10 g) over 60 minutes and the mixture was stirred at the same temperature for 120 minutes. The resulting crystals were separated by filtration and the crystals were washed with acetone (100 ml) and then dried at 70° C. under reduced pressure for 3 hours to give the title compound as white crystals (47.8 g, yield 92%) (crystal B2) which exhibit more excellent storage stability than crystal B1 obtained in Example 3.

mp 165–178° C.;

Mass (CI, m/z): 374 (M$^+$+1);

IR (KBr) $v_{max}$cm$^{-1}$: 1758, 1690.

Example 5

2-Acetoxy-5-(α-cyclopropylcarbonyl-2-fluorobenzyl)-4,5,6,7-tetrahydrothieno[3,2-c]pyridine maleate To a solution of maleic acid (932 g) in acetone (15 L) heated to 40° C. was added 2-acetoxy-5-(α-cyclopropylcarbonyl-2-fluorobenzyl)-4,5,6,7-tetrahydrothieno[3,2-c]pyridine (3000 g) obtained in Reference example 1. The mixture was stirred at room temperature for 2 hours. The resulting crystals were separated by filtration and washed with acetone (4 L) and then dried at 60° C. under reduced pressure for 8 hours to give the title compound as white crystals (3538 g, yield 90%)

mp: 172–173° C.;

Mass (CI, m/z): 374 (M$^+$+1);

IR (KBr) $v_{max}$cm$^{-1}$: 1782, 1713.

Example 6

2-Acetoxy-5-(α-cyclopropylcarbonyl-2-fluorobenzyl)-4,5,6,7-tetrahydrothieno[3,2-c]pyridine hydrochloride (crystal B2)

To a solution of 2-acetoxy-5-(α-cyclopropylcarbonyl-2-fluorobenzyl)-4,5,6,7-tetrahydrothieno[3,2-c]pyridine (50 g) obtained in Reference example 1 in acetone (750 ml) was added dropwise concentrated hydrochloric acid (36%, 6.78 g) over 5 minutes with stirring at 55° C. Crystals of B1 (0.1 g) obtained in Example 3 were added to the reaction mixture as seed crystals and the resulting mixture was stirred at the same temperature for 60 minutes. To the resulting mixture was further added dropwise concentrated hydrochloric acid (36%, 6.08 g) over 60 minutes and the mixture was stirred at the same temperature for 120 minutes. The resulting crystals were separated by filtration and the crystals were washed with acetone (100 ml) and then dried at 70° C. under reduced pressure for 3 hours to give the title compound as white crystals (46.2 g, yield 89%) (crystal B2).

mp: 164–178° C.;

Mass (CI, m/z): 374 (M$^+$+1);

IR (KBr) $v_{max}$cm$^{-1}$: 1758, 1690.

Reference Example 1

2-Acetoxy-5-(α-cyclopropylcarbonyl-2-fluorobenzyl)-4,5,6,7-tetrahydrothieno[3,2-c]pyridine (a) Cyclopropyl 2-fluorobenzyl ketone To a suspension of magnesium powder (7.2 g) in anhydrous diethyl ether (60 ml) was added a solution of 2-fluorobenzylbromide (30 ml) in diethyl ether (30 ml), then the mixture was stirred at room temperature for 1 hour. The reaction mixture was added dropwise to a solution of cyclopropyl cyanide (18.2 ml) in diethyl ether (120 ml) over 100 minutes. After stirring for 30 minutes at room temperature the stirred mixture was heated under reflux for 1 hour. After the reaction, the reaction mixture was partitioned between ethyl acetate and saturated aqueous ammonium chloride solution. The ethyl acetate layer was washed successively with water, saturated aqueous sodium bicarbonate solution, and saturated aqueous sodium chloride solution, then dried over anhydrous sodium sulfate, and then evaporated under reduced pressure. The residue was purified by chromatography on a silica gel column using toluene as the eluant to afford the desired product (23 g containing solvent) as a yellow liquid.

$^1$H NMR (CDCl$_3$) δppm: 0.82–0.98 (2H, m), 1.03–1.17 (2H, m), 1.92–2.06 (1H, m), 3.86 (2H, s), 7.10–7.30 (4H, m);

Mass (CI, m/z): 179 (M$^+$+1).

(b) 5-(α-Cyclopropylcarbonyl-2-fluorobenzyl)-2-oxo-2,4,5,6,7,7a-hexahydrothieno[3,2-c]pyridine To a solution of cyclopropyl 2-fluorobenzyl ketone (8.7 g) obtained in Reference example 1(a) in carbon tetrachloride (80 ml) was added N-bromosuccinimide (9.6 g) and benzoyl peroxide (0.5 g), then the mixture was heated under reflux for 6 hours. After the reaction, toluene was added to the reaction mixture and the resulting solid was filtered off. The filtrate was concentrated under reduced pressure. The residue was purified by chromatography on a silica gel column using toluene as the eluant to afford α-cyclopropylcarbonyl-2-fluorobenzyl bromide (8.5 g) as a yellow oil.

To a solution of α-cyclopropylcarbonyl-2-fluorobenzyl bromide (6.0 g) obtained above in dimethylformamide (20 ml) was added 2-oxo-2,4,5,6,7,7a-hexahydrothieno[3,2-c]pyridine hydrochloride (4.8 g), which was prepared according to the method described in EP 192535 (Japanese Patent Application Publication No. Sho 61-246186) and potassium bicarbonate (7.0 g). After stirring the mixture at room temperature for 2 hours the reaction mixture was partitioned between ethyl acetate and water. The ethyl acetate layer was washed with saturated aqueous sodium chloride solution, then dried over anhydrous magnesium sulfate, and evaporated under reduced pressure. After purification of the residue by chromatography on a silica gel column using toluene/ethyl acetate=3/1 as the eluant, the product was crystallized from diisopropyl ether to afford the desired product (2.6 g, yield 35%) as pale brown crystals.

mp: 123–125° C.;

$^1$H NMR (CDCl$_3$) δppm: 0.75–0.96 (2H, m), 0.99–1.14 (2H, m), 1.83–2.01 (1H, m), 2.02–2.17 (1H, m), 2.25–2.45 and 2.47–2.62 (total 2H, each m), 2.85 and 3.10 (total 2H, each d, J=12.0 Hz), 3.88–4.01 and 4.03–4.16 (total 2H, each m), 4.85 and 4.89 (total 1H, each s), 6.03 and 6.06 (total 1H, each s), 7.10–7.45 (4H, m);

Mass (CI, m/z):332 (M$^+$+1), 262;

Anal Calcd. for $C_{18}H_{18}FNO_2S$: C,65.23; H,5.48; N,4.23 Found: C,65.09; H,5.55; N,4.20.

(c) 2-Acetoxy-5-(α-cyclopropylcarbonyl-2-fluorobenzyl)-4,5,6,7-tetrahydrothieno[3,2-c]pyridine To a solution of 5-(α-cyclopropylcarbonyl-2-fluorobenzyl)-2-oxo-2,4,5,6,7,7a-hexahydrothieno[3,2-c]pyridine (2.6 g) obtained in reference example 1(b) in a mixture of dimethylformamide (10 ml) and acetic anhydride (5 ml), cooled in an ice bath, was added sodium hydride (60% dispersion in mineral oil, 0.35 g), then the mixture was stirred at the same temperature for 30 minutes, and then at room temperature for 3 hours. After the reaction, the mixture was extracted with ethyl acetate and the extract was washed with saturated aqueous sodium chloride solution, then dried over anhydrous sodium sulfate, and concentrated under reduced pressure. After purification of the residue by chromatography on a silica gel column using toluene/ethyl acetate=3/1 as the eluant, the product was crystallized from diisopropyl ether to afford the title compound (1.88 g, yield 65%) as white crystals.

mp: 120–122° C.;

$^1$H NMR (CDCl$_3$) δppm: 0.80–0.95 (2H, m), 0.99–1.16 (2H, m), 2.27 (3H, s), 2.21–2.34 (1H, m), 2.70–2.95 (4H, m), 3.47 (1H, d, J=15.0 Hz), 3.57 (1H, d, J=15.0 Hz), 4.83 (1H, s), 6.27 (1H, s), 7.10–7.55 (4H, m);

IR (KBr) ν$_{max}$cm$^{-1}$: 1758, 1704;

Mass (CI, m/z): 374 (M$^+$+1), 304;

Anal Calcd. for C$_{20}$H$_{20}$FNO$_3$S: C,64.32; H,5.40; N,3.75 Found: C,64.46; H,5.39; N,3.73.

Test Example 1

Plasma Concentration of a Metabolite in Dogs

After oral administration of the test compound to male beagle dogs (about 10 kg in body weight, purchased from Kasho Co., Ltd. and Nippon Nosan Kogyo K.K.), the plasma concentration of a metabolite was measured. (2Z)-[1-[α-cyclopropylcarbonyl-2-fluorobenzyl]-4-methyothio-3-piperidinylidene]acetic acid (hereinafter referred to as "S-methyl form") was used as a reference metabolite. This S-methyl form is a major metabolite of 2-acetoxy-5-(α-cyclopropylcarbonyl-2-fluorobenzyl)-4,5,6,7-tetrahydrothieno[3,2-c]pyridine in human, dog or rat plasma. It has already been reported that the S-methyl form would be an index of the amount of an active metabolite of 2-acetoxy-5-(α-cyclopropylcarbonyl-2-fluorobenzyl)-4,5,6,7-tetrahydrothieno[3,2-c]pyridine, because it is formed by a further successive metabolism of an active metabolite [*Annu. Rep. Sankyo Res. Lab.*, 51, 1(1999)].

Thirty minutes after feeding dog chow, each test compound (10 mg/kg) filled in a gelatin capsule was orally administered to each dog. Three ml of a blood sample was withdrawn with a heparin-treated syringe from the brachial saphenous vein of each dog at 15, 30, 45, 60, 90 and 120 minutes after the administration. Immediately after the sample collection, the whole blood was centrifuged to obtain the plasma. Plasma samples were stored at −30° C. until analysis. To 0.5 ml of thawed plasma was added 0.25 ml of 2-hydroxyacetophenone (1 µg/ml, as an internal standard substance), 0.25 ml of 10 mM potassium phosphate buffer (pH 4.5) and 0.5 ml of methanol. The mixture was stirred at 20±3° C.

After addition of 8 ml of isopropyl alcohol/chloroform mixture (1/9), the mixture was shaken to extract the S-methyl form and the internal standard substance into the solvent phase. The extract was separated into an aqueous phase and a solvent phase using low-speed centrifugation (1500×g, for 15 minutes). An appropriate aliquot of the underlying solvent phase was dried to dryness using nitrogen gas and was then redissolved in 0.25 ml of HPLC mobile phase. Separately, a known amount of the S-methyl form was added to the control dog plasma, followed by similar extraction. The calibration curve was constructed by plotting the ratio of the peak areas of the S-methyl form and the internal standard substance on the Y axis against the corresponding concentration of added S-methyl form on the X axis. The concentration of the S-methyl form in the sample was calculated from the calibration curve.

HPLC Conditions

Column: YMC A302 (4.6×150 mm)

Mobile phase: acetonitrile/isopropyl alcohol/water/trifluoroacetic acid (10/12/78/0.01)

Flow rate: 1.0 ml/min

Detection: UV 220 nm

Injected amount: 30 µl

The results are shown in Table 1. In this table, the area under the plasma concentration—time curve, which is an index of the amount produced in vivo, and the maximum plasma concentration, which are pharmacokinetic parameters, are abbreviated as AUC and Cmax, respectively. In this table, the term "hydrochloride" means 2-acetoxy-5-(α-cyclopropylcarbonyl-2-fluorobenzyl)-4,5,6-7-tetrahydrothieno[3,2-c]pyridine hydrochloride obtained in Example 1, while "free form" means 2-acetoxy-5-(α-cyclopropylcarbonyl-2-fluorobenzyl)-4,5,6,7-tetrahydrothieno[3,2-c]pyridine.

TABLE 1

Pharmacokinetic parameters (mean ± standard deviation) of the S-methyl form in the plasma after oral administration to dogs

| Test compound | n | AUC (µg.min/ml) | Cmax (µg/ml) |
| --- | --- | --- | --- |
| Hydrochloride | 4 | 74.1 ± 25.8 | 1.09 ± 0.26 |
| Free form | 3 | 36.4 ± 8.2 | 0.615 ± 0.141 |

The results indicate that both the AUC and the Cmax values are increased by conversion of 2-acetoxy-5-(α-cyclopropylcarbonyl-2-fluorobenzyl)-4,5,6,7-tetrahydrothieno[3,2-c]pyridine into its hydrochloride.

Test Example 2

Inhibitory Effect on Platelet Aggregation (Feeding)

For this test, male beagle dogs (about 10 kg in body weight, purchased from Kasho Co., Ltd. and Nippon Nosan Kogyo K.K.) were used. One group consisted of 5 or 6 dogs. The platelet aggregation was measured using an automatic platelet aggregometer ("PAM-6C", trade name; a product of Mebanix Corporation) in accordance with the method of Born, et al. (*J. Physiol.*, 168, 178 (1963)) with a partial modification.

Each of 2.5 hours and 4.5 hours after feeding, 5.4 ml of blood was collected from the cephalic vein of each dog using sodium citrate (0.6 ml, 3.8% (w/v)) as an anticoagulant. The citrate-added blood was centrifuged (240 g, 20 minutes) to separate platelet-rich plasma (hereinafter referred to as "PRP") and platelet-poor plasma (hereinafter referred to as "PPP"). After the number of platelets in PRP was counted by an automatic hematology analyzer ("K-1000", trade name; a product of Sysmex Corporation), PPP was added to adjust the number of platelets to 3×10$^8$/ml. PRP (240 µl) dispensed in a cuvette was set on the automatic platelet aggregometer. After preheating (at 37° C.) for 1 minute, 10 µl of ADP (final concentration: 20 µM) was added to cause platelet aggregation. For 10 minutes, platelet aggregation was measured and the maximum aggregation was determined to give the pre-administration value.

On the next day, 30 minutes after feeding, each test compound filled in a gelatin capsule was orally administered to the dogs. The blood was collected each of 2 and 4 hours after the administration. The platelet aggregation of PRP was measured, whereby the maximum aggregation was determined. The inhibition (%) of platelet aggregation by the test compound was calculated by comparing it with the pre-administration value. The results are shown in Tables 2 and 3.

In these tables, the term "hydrochloride" means 2-acetoxy-5-(α-cyclopropylcarbonyl-2-fluorobenzyl)-4,5,6-7-tetrahydrothieno[3,2-c]pyridine hydrochloride obtained in Example 1, "free form" means 2-acetoxy-5-(α-cyclopropylcarbonyl-2-fluorobenzyl)-4,5,6,7-tetrahydrothieno[3,2-c]pyridine, and "maleate" means 2-acetoxy-5-(α-cyclopropylcarbonyl-2-fluorobenzyl)-4,5,6,7-tetrahydrothieno[3,2-c]pyridine maleate obtained in Example 2.

TABLE 2

Inhibition of platelet aggregation (mean ± standard deviation) after oral administration to dogs

| Test compound | Dose (mg/kg) | n | Inhibition (%) of platelet aggregation | |
|---|---|---|---|---|
| | | | 2 hours | 4 hours |
| Hydrochloride | 0.3 | 5 | 49.0 ± 18.7 | 48.5 ± 18.3 |
| Free form | 0.3 | 5 | 25.8 ± 10.9 | 28.6 ± 14.2 |

TABLE 3

Inhibition of platelet aggregation (mean ± standard deviation) after oral administration to dogs

| Test compound | Dose (mg/kg) | n | Inhibition (%) of platelet aggregation | |
|---|---|---|---|---|
| | | | 2 hours | 4 hours |
| Maleate | 0.3 | 6 | 50.9 ± 14.5 | 58.6 ± 15.7 |
| Free form | 0.3 | 6 | 21.7 ± 9.8 | 23.8 ± 12.6 |

Test Example 3

Inhibitory Effect on Platelet Aggregation (Fasting)

For this test, male beagle dogs (about 10 kg in body weight, purchased from Kasho Co., Ltd. and Nippon Nosan Kogyo K.K.) were used. One group consisted of 3 dogs. The platelet aggregation was measured using an automated platelet aggregometer ("PAM-6C", trade name; a product of Mebanix Corporation) in accordance with the method of Born, et al. (*J. Physiol.*, 168, 178(1963)) with a partial modification.

From the cephalic vein of each dog fasted overnight, 5.4 ml of the blood was collected using sodium citrate (0.6 ml, 3.8% (w/v)) as an anticoagulant. The resulting citrate-added blood was centrifuged (240 g, 20 minutes) to separate platelet-rich plasma (hereinafter referred to as "PRP") and platelet-poor plasma (hereinafter referred to as "PPP"). After the number of platelets in PRP was counted by an automatic hematology analyzer ("K-1000", trade name; a product of Sysmex Corporation), PPP was added to adjust the number of platelets to $3 \times 10^8$/ml. PRP (240 μl) dispensed in a cuvette was set on the automatic platelet aggregometer. After pre-heating (at 37° C.) for 1 minute, 10 μl of ADP (final concentration: 20 μM) was added to cause platelet aggregation. For 10 minutes, platelet aggregation was measured and the maximum aggregation was determined to give the pre-administration value.

On the next day, each test compound filled in a gelatin capsule was orally administered to the dogs. The blood was collected each of 2 and 4 hours after administration. The platelet aggregation of PRP was measured, whereby the maximum aggregation was determined. The inhibition (%) of platelet aggregation by the test compound was calculated by comparing it with the pre-administration value. The results are shown in Table 4.

In this table, the term "maleate" means 2-acetoxy-5-(α-cyclopropylcarbonyl-2-fluorobenzyl)-4,5,6,7-tetrahydrothieno[3,2-c]pyridine maleate obtained in Example 2, while the term "free form" means 2-acetoxy-5-(α-cyclopropylcarbonyl-2-fluorobenzyl)-4,5,6,7-tetrahydrothieno[3,2-c]pyridine.

TABLE 4

Inhibition of platelet aggregation (mean ± standard deviation) after oral administration to dog

| Test compound | Dose (mg/kg) | n | Inhibition (%) of platelet aggregation | |
|---|---|---|---|---|
| | | | 2 hours | 4 hours |
| Maleate | 1.0 | 3 | 63.4 ± 22.9 | 88.5 ± 5.7 |
| Free form | 1.0 | 3 | 27.9 ± 24.8 | 28.7 ± 24.4 |

The results of Tests 2 and 3 indicate that the inhibitory effect of 2-acetoxy-5-(α-cyclopropylcarbonyl-2-fluorobenzyl)-4,5,6-7-tetrahydrothieno[3,2-c]pyridine hydrochloride and maleate on ADP-induced platelet aggregation is stronger than that of 2-acetoxy-5-(α-cyclopropylcarbonyl-2-fluorobenzyl)-4,5,6,7-tetrahydrothieno[3,2-c]pyridine, and 2-acetoxy-5-(α-cyclopropylcarbonyl-2-fluorobenzyl)-4,5,6-tetrahydrothieno[3,2-c]pyridine hydrochloride and maleate both demonstrate superior pharmacological activity to 2-acetoxy-5-(α-cyclopropylcarbonyl-2-fluorobenzyl)-4,5,6,7-tetrahydrothieno[3,2-c]pyridine.

Formulation Example 1

Hard Capsule

2-Acetoxy-5-(α-cyclopropylcarbonyl-2-fluorobenzyl)-4,5,6,7-tetrahydrothieno[3,2-c]pyridine hydrochloride powder (50 mg), lactose (128.7 mg), cellulose (70 mg) and magnesium stearate (1.3 mg) are blended, passed through a sieve (60 mesh), and filled into a hard gelatin capsule (No. 3, 250 mg).

Formulation Example 2

Tablet

2-Acetoxy-5-(α-cyclopropylcarbonyl-2-fluorobenzyl)-4,5,6,7-tetrahydrothieno[3,2-c]pyridine hydrochloride powder (50 mg), lactose (124 mg), cellulose (25 mg) and magnesium stearate (1 mg) are mixed, and compressed by a tablet machine to yield a tablet weighing 200 mg which, if desired, may be coated.

Formulation Example 3

Hard Capsule

2-Acetoxy-5-(α-cyclopropylcarbonyl-2-fluorobenzyl)-4,5,6,7-tetrahydrothieno[3,2-c]pyridine maleate powder (50 mg), lactose (128.7 mg), cellulose (70 mg) and magnesium stearate (1.3 mg) are blended, passed through a sieve (60 mesh), and filled into a hard gelatin capsule (No. 3, 250 mg).

Formulation Example 4

Tablet

2-Acetoxy-5-(α-cyclopropylcarbonyl-2-fluorobenzyl)-4,5,6,7-tetrahydrothieno[3,2-c]pyridine maleate powder (50 mg), lactose (124 mg), cellulose (25 mg) and magnesium stearate (1 mg) are mixed, and compressed by a tablet machine to yield a tablet weighing 200 mg, which, if desired, may be coated.

What is claimed is:

1. 2-Acetoxy-5-(α-cyclopropylcarbonyl-2-fluorobenzyl)-4,5,6,7-tetrahydrothieno[3,2-c]pyridine hydrochloride.

2. 2-Acetoxy-5-(α-cyclopropylcarbonyl-2-fluorobenzyl)-4,5,6,7-tetrahydrothieno[3,2-c]pyridine maleate.

3. A medicament composition comprising a pharmaceutically effective amount of the salt according to claim 1 as an active ingredient in combination with a pharmaceutically acceptable carrier.

4. A medicament composition comprising a pharmaceutically effective amount of the salt according to claim 2 as an active ingredient in combination with a pharmaceutically acceptable carrier.

5. The medicament composition according to claim 3, wherein said medicament is for prevention or treatment of a thrombus formation-induced or an embolization-induced disease in a warm blooded animal.

6. The medicament composition according to claim 4, wherein said medicament is for prevention or treatment of a thrombosis or an embolism in a human.

7. The medicament composition according to claim 6, wherein said medicament is for treatment of a thrombosis or an embolism in a human.

8. A method for prevention or treatment of a thrombus formation-induced or an embolization-induced disease in a warm blooded animal which comprises administering an effective amount of the salt according to claim 1.

9. The method according to claim 8, wherein the warm blooded animal is a human.

10. The method according to claim 9, wherein the method is for treatment of a thrombosis.

11. The method according to claim 9, wherein the method is for treatment of an embolism.

12. A method for prevention or treatment of a thrombus formation-induced or an embolization-induced disease in a warm blooded animal which comprises administering an effective amount of the salt according to claim 2.

13. The method according to claim 12, wherein the warm blooded animal is a human.

14. The method according to claim 13, wherein the method is for treatment of a thrombosis.

15. The method according to claim 13, wherein the method is for treatment of an embolism.

* * * * *

UNITED STATES PATENT AND TRADEMARK OFFICE
CERTIFICATE OF CORRECTION

PATENT NO.     : 6,693,115 B2
DATED          : February 17, 2004
INVENTOR(S)    : Asai et al.

It is certified that error appears in the above-identified patent and that said Letters Patent is hereby corrected as shown below:

<u>Column 14,</u>
Line 1, after "claim" delete "6" and insert -- 5 --.

Signed and Sealed this

Twenty-first Day of June, 2005

JON W. DUDAS
*Director of the United States Patent and Trademark Office*

Disclaimer

6,693,115 B2 — Fumitoshi Asai, Tanashi (JP); Taketoshi Ogawa, Tokyo (JP); Hideo Naganuma, Tokyo (JP); Naotoshi Yamamura, Nishitokyo (JP); Teruhiko Inoue, Ube (JP); Kazuyoshi Nakamura, Onoda (JP). ACID ADDITION SALTS OF HYDROPYRIDINE DERIVATIVES. Patent dated March 27, 2012. Disclaimer filed February 17, 2004, by the assignee, Ube Industries, Ltd. and Daiichi Sankyo Company, Limited.

Hereby disclaims the complete claims in said patent, 1-15.

*(Official Gazette, August 19, 2014)*